United States Patent [19]
Wong et al.

[11] Patent Number: 5,843,741
[45] Date of Patent: Dec. 1, 1998

[54] METHOD FOR ALTERING THE DIFFERENTIATION OF ANCHORAGE DEPENDENT CELLS ON AN ELECTRICALLY CONDUCTING POLYMER

[75] Inventors: Joyce Y. Wong, Cambridge; Donald E. Ingber, Boston; Robert S. Langer, Newton, all of Mass.

[73] Assignees: Massachusetts Insitute of Technology, Cambridge; Children's Medical Center Corporation, Boston, both of Mass.

[21] Appl. No.: 283,402

[22] Filed: Aug. 1, 1994

[51] Int. Cl.$^6$ ................................................ C12N 13/00
[52] U.S. Cl. ........................................................ 435/173.8
[58] Field of Search ........................................... 435/173.8

[56] References Cited

U.S. PATENT DOCUMENTS

| | | | |
|---|---|---|---|
| 3,871,961 | 3/1975 | Gianessi | 435/173.8 |
| 4,085,254 | 4/1978 | Atkins | 429/2 |
| 4,164,794 | 8/1979 | Spector et al. | 623/16 |
| 4,491,605 | 1/1985 | Mazurek et al. | 427/525 |
| 4,521,450 | 6/1985 | Bjorkland et al. | 427/121 |
| 4,604,427 | 8/1986 | Roberts et al. | 528/185 |
| 4,687,808 | 8/1987 | Jarrett et al. | 525/54.1 |
| 4,969,468 | 11/1990 | Byers et al. | 128/642 |
| 4,983,322 | 1/1991 | Elsenbaumer | 250/500 |
| 5,056,518 | 10/1991 | Pethica et al. | 607/2 |
| 5,120,829 | 6/1992 | Pierschbacher et al. | 530/326 |
| 5,134,070 | 7/1992 | Casnig | 435/173.6 |
| 5,134,177 | 7/1992 | Aklonis et al. | 523/201 |
| 5,143,089 | 9/1992 | Alt | 607/121 |
| 5,310,469 | 5/1994 | Cunningham et al. | 204/403 |
| 5,312,620 | 5/1994 | Ribi | 424/78.31 |

FOREIGN PATENT DOCUMENTS

| | | | |
|---|---|---|---|
| 0 472 990 A2 | 8/1991 | European Pat. Off. | |
| 4026978 A1 | 8/1990 | Germany | |
| 8702705 | 5/1987 | WIPO | 435/173.8 |
| WO 88/03785 | 6/1988 | WIPO | |
| 8903876 | 5/1989 | WIPO | 435/173.8 |
| WO 89/04849 | 6/1989 | WIPO | |
| WO 92/11644 | 7/1992 | WIPO | |

OTHER PUBLICATIONS

Alberts, B., et al., *Molecular Biology of the Cell*, 2nd ed. New York: Garland Publishing Co. pp. 727–738 (1989).

Andreatta, A. and P. Smith, "Processing of Conductive Polyanilline–UHMW Polyethylene Blends from Solutions in Non–Polar Solvents", *Synth. Met.*, 55(2 and 3):1017–1022 (1993).

Armes, S. P., "Optimum reaction conditions for the Polymerization of Pyrrole by Iron (III) Chloride in Aqueous Solution", *Synthetic Metals*, 20:365–371 (1987).

Baier, R. E., et al., "Adhesion: Mechanisms That Assist or Impede It", *Science*, 162:1360–1368 (1968).

Ben Ze'ev, A., et al., "Cell–cell and cell–matrix interactions differentially regulate the expression of hepatic and cytoskeletal genes in primary cultures of rat hepatocytes", *Proc. Natl. Acad. Sci. USA*, 85:2161–2165 (1988).

Ben Ze'ev, A., et al., "Protein Synthesis Requires Cell–Surface Contact while Nuclear Events Respond to Cell Shape in Anchorage–Dependent Fibroblasts", *Cell*, 21:365–372 (1980).

Bissell, D. M. and M. O. Choun, "The Role of Extracellular Matrix in Normal Liver", *Scand. J. Gastroenterol.*, 23:1–7 (1988).

Bissell, D. M., et al., "Support of Cultured Hepatocytes by a Laminin–rich Gel", *J. Clin. Invest.*, 79:801–812 (1987).

Bourdillon, C., et al., "Covalent Linkage of Glucose Oxidase on Modified Glassy Carbon Electrodes. Kinetic Phenomena", *Journal of the American Chemical Society*, 102(12):4231–4235 (1980).

Bull, R. A., et al., "Polymer Films on Electrodes VII. Electrochemical Behavior of Polypyrrole–Coated Platinum and Tantalum Electrodes", *J. Electrochem Soc.*, 129(5):1009–1015 (1982).

Bull, R. A., et al., "Polymer Films on Electrodes 13. Incorporation of Catalysts into Electronically Conductive Polymers: Iron Phthalocyanine in Polypyrrole", *J. Electrochem. Soc.*, 130(7):1636–1638 (1983).

Burgmayer, P. and R. W. Murray, "Ionic Conductivity of Polypyrrole", *Handbook of Conducting Polymers*. New York: Marcel Dekker, Inc., 1:507–523.

Cao, Y., et al., "Counter–ion induced processibility of conducting polyaniline and of conducting polyblends of polyaniline in bulk polymers", *Synth. Met.*, 48:91–97 (1992).

Cao, Y. and A. J. Heeger, "Magnetic susceptibilty of polyaniline in solution in non–polar organic solvents and in polyblends in poly(methyl methacrylate)", *Synthetic Metals*, 52:193–200 (1992).

Cohen, S., et al., "A Native 170,000 Epidermal Growth Factor Receptor–Kinase Complex from Shed Plasma Membrane Vesicles", *The Journal of Biological Chemistry*, 357(3):1523–1531 (1982).

Couchman, J. R., et al., "Fibronectin Has a Dual Role in Locomotion and Anchorage of Primary Chick Fibroblasts and Can Promote Entry into the Division Cycle", *The Journal of Cell Biology*, 93:402–410 (1982).

Decher, G., et al., "Buildup of ultrathin multilayer films by a sefl–assembly process: III. Consecutively alternating adsorption of anionic and cationic polyelectrolytes on charged surfaces", *Thin Solid Films*, 210/211 (1–2):831–835 (1992).

Denk, H. and E. Lackinger, "Cytoskeleton in Liver Diseases", *Sem. Liver Disease*, 6(3):199–211 (1986).

Diaz, A. F. and K. K. Kanazawa, "Electrochemical Polymerization of Pyrrole", *J. C. S. Chem. Comm.*, 635–636 (1979).

(List continued on next page.)

*Primary Examiner*—Jon P. Weber
*Attorney, Agent, or Firm*—Arnall Golden & Gregory, LLP.

[57] ABSTRACT

Described is a method and cell culture system for altering the proliferation, differentiation, or function of anchorage dependent cells which includes associating the cells with a surface formed of an electrically conducting polymer and applying an effective amount of a voltage to change the oxidation state of the polymer without damaging the cells.

26 Claims, 2 Drawing Sheets

OTHER PUBLICATIONS

Diaz, A. F. and K. K. Kanazawa, "Polypyrrole: An Electrochemical Approach to Conducting Polymers", *Extended Linear Chain Compounds*, ed. Joel S. Miller. New York: Plenum Press, pp. 417–441.

Ewing, A. G., et al., "Permeation of Neutral, Cationic, and Anionic Electrode Reactants through a Polycationic Polymer Film as a Function of Electrolyte Concentration", *J. Phys. Chem.*, 89(7):1263–1269 (1985).

Feldberg, S. W., "Reinterpretation of Polypyrole Electrochemistry. Consideration of Capacitive Currents in Redox Switching of Conducting Polymers", *J. Am. Chem. Soc.*, 106(17):4671–4674 (1984).

Folkman, J. and A. Moscona, "Role of Cell Shape in Growth Contol", *Nature*, 273:345–349 (1978).

Gabridge, M. G., "The Chamber/Dish: An Improved Vessel for Cell and Explant Culture", In Vitro, 17(2):91–97 (1981).

Genies, E. M. and J. M. Pernaut, "Characterization of the Radical Cation and the Dication Species of Polypyrrole by Spectroelectrochemistry: Kinetics, Redox Properties, and Structural Changes upon Electrochemical Cycling", *J. Electroanal. Chem.*, 191(1):111–126 (1985).

Giaever, I. and C. R. Keese, "Monitoring fibroblast behavior in tissue culture with an applied electric field", *Proc. Natl. Acad. Sci. USA.*, 81:3761–3764 (1984).

Gregory, R. V., et al., "Conductive Textiles", *Synthetic Metals*, 28(1 and 2):C823–C835 (1989).

Grinnell F., "Cellular Adhesiveness and Extracellular Substrata", *International Review of Cytology*, eds. Bourne, G. H., et al. New York: Academic Press, 53:65–144 (1978).

Gulberg, E. L., et al., "Amperometric systems for the determination of oxidase enzyme dependent reactions by continous flow and flow injection analysis", *Journal of Automatic Chemistry*, 2(4):189–194 (1980).

Harris, et al., "Silicone Rubber Substrata: A New Wrinkle in the Study of Cell Locomotion", *Science*, 208:177–179 (1980).

Hynes, R. O., "Integrins: A Family of Cell Surface Receptors", *Cell*, 48:549–554 (1987).

Hyodo, K. and A. G. Macdiarmid, "Effect of Sulphate Ion on the Electrochemical Polymerization of Pyrrole and N–Methylpyrrole", *Synthetic Metals*, 11:167–176 (1985).

Ingber, D. E., "Fibronectin controls capillary endothelial cell growth by modulating cell shape", *Proc. Natl. Acad. Sci. USA.* 87:3579–3583 (1990).

Ingber, D. E. and J. D. Jamieson, "Cells as Tensegrity Structures: Architectural Regulation of Histodifferentiation by Physical Forces Transduced over Basement Membrane", *Gene Expression During Normal and Malignant Differentiation*, eds. L. C. Anderson, et al., Orlando: Academic Press. pp. 13–32 (1985).

Ingber, D. E., et al., "Endothelial Growth Factors and Extracellular Matrix Regulate DNA Synthesis through Modulation of Cell and Nuclear Expansion", In Vitro *Cell Dev. Biol*, 23(5):387–394 (1987).

Ingber, D. E. and J. Folkman, "Mechanochemical Swithcing between Growth and Differentiation during Fibroblast Growth Factor–stimulated Angiogenesis In Vitro: Role of Extracellular Matrix", *J. Cell Biol.*, 109:317–330 (1989).

Ingber, D. E. and J. Folkman, "Tension and Compression as Basic Determinants of Cell Form and Function: Utilization of a Cellular Tensegrity Mechanism", *Cell Shape: Determinants, Regulation, and Regulatory Role*, eds. W. D. Stein and F. Bronner. California: Academic Press, pp. 3–31 (1989).

Iseki, M., et al., "Electrochemical exchange process of dopant anions in polypyrrole", *Synthetic Metals*, 40(1):117–126 (1991).

Jauregui, H. O., et al., "Attachment and Long Term Survival of Adult Rat Hepatocytes in Primary Monolayer Cultures: Comparison of Different Substrata and Tissue Culture Media Formulations", In Vitro *Cell Dev. Bio.*, 22(1):13–22 (1986).

Juliano, R. L. and S. Haskill, "Signal Transduction from the Extracellular Matrix", *The Journal of Cell Biology*, 120(3):577–585 (1993).

Kanatzidis, M. G., "Conductive Polymers", *Chemical & Engineering News*, 36–54 (Dec. 3, 1990).

Kanazawa, K. K., et al., "'Organic Metals': Polypyrrole, a Stable Synthetic 'Metallic' Polymer", *J. C. S. Chem. Comm.*, 854–855 (1979).

Kanazawa, K. K., et al., "Polypyrrole: An Electrochemically Synthesized Conducting Organic Polymer", *Synthetic Metals*, 1:329–336 (1979/1980).

Kleinman, H. K., et al., "Use of Extracellular Matrix Components for Cell Culture", *Anal Biochem.*, 166:1–13 (1987).

Kleinsmith, et al., "The Cell Division Cycle", *Principles of Cell Biology*. New York: Harper & Row Publishers, INc. pp. 490–537 (1988).

Landry, J., et al., "Spheroidal Aggregate Culture of Rat Liver Cells: Histotypic Reorganization, Biomatrix Deposition, and Maintenance of Functional Activities", *J. Cell Bio.*, 101:914–923, (1985).

Lavine, L. S. and A. J. Grodzinsky, "Current Concepts Review Electrical Stimulation of Repair of Bone", *The Journal of Bone and Joint Surgery*, 69(4):625–630 (1987).

Li, M. L., et al., "Influence of a reconstituted basement membrane and its components on casein gene expression and secretion in mouse mammary epithelial cells", *Proc. Natl. Acad. Sci.*, 84:136–140 (1987).

Li, Y. and R. Qian, "Effect of Anion and Solution pH on the Electrochemical Behavior of Polypyrrole in Aqueous Solution", *Synthetic Metals*, 28(1 and 2):C127–132 (1989).

Liao, Y. H. and K. Levon, "Polymeric Dopants for Polyaniline", *PSME*, 69:327–328 (1993).

Malhotra, B. D., et al., "Polyaniline/Polymeric Acid Composite, a Novel Conducting Rubber", *J. Appl. Polym. Sci.*, 40:1049–1052 (1990).

Malmstadt, H. V. and H. L. Pardue, "Quantitative Analysis by an Automatic Potentiometric Reaction Rate Method", *Analytical Chemistry*, 33(8):1040–1047 (1961).

McKenna, N. M. and Y. L. Wang, "Culturing Cells on the Miscroscope Stage", *Methods in Cell Biology*, 29:195–205 (1989).

Meierhenry, E. F., et al., "Dieldrin–Induced Mallory Bodies in Hepatic Tumors of Mice of Different Strains", *Hepatology*, 3(1):90–95 (1983).

Michalopoulos, G. and H. C. Pitot, "Primary Culture on Parenchymal Liver Cells on Collagen Membrane", *Exp. Cell Res.*, 94:70–78 (1975).

Miller, L. L., "Electrochemically Controlled Released of Drug Ions from Conducting Polymers", *Mol. Cryst. Lig. Cryst.*, 160:297–301 (1988).

Minehan, D. S., et al., "Kinetics of DNA Binding to Polypyrrole", *PMSE*, 64:341–342 (1991).

Mooney, D. J. and R. Langer, "Induction of Hepatocyte Differentiation by the Extracellular Matrix and an RGD–Containing Synthetic Peptide", *Mat. Res. Soc. Symp.*, 252:199–204 (1992).

Mooney, D., et al., "Switching from Differentiation to Growth in Hepatocytes: Control by Extracellular Matrix", *Journal of Cellular Physiology*, 151:497–505 (1992).

Myers, R. E., "Chemical Oxidative Polymerization as a Synthetic Route to Electrically Conducting Polypyrroles", *Journal of Electronic Materials*, 15(2):61–69 (1986).

Prezyna, L. A., et al, "Interaction of Cationic Polypeptides with Electroactive Polypyrrole/Poly(Styrenesulfonate) and Poly(N–methylpyrrole)/Poly(styrenesulfonate) Films", *Macromolecules*, 24(19):5283–5287 (1991).

Qian, R. and J. Qiu, "Electrochemically Prepared Polypyrroles from Aqueous Solutions", *Polymer Journal*, 19(1):157–172 (1987).

Satoh, M., et al., "Highly Conducting Polypyrrole Prepared by Electrochemical Oxidation Method in Aqueous Solution", *Japanese Journal of Applied Physics*, 24(6):L423–L424 (1985).

Sawada, N., et al., "Effects of Extracellular Matrix Components on the Growth and Differentiation of Cultured Rat Hepatocytes", In Vitro *Cell Dev. Bio.*, 23(4):267–273 (1987).

Scott, J. C., et al., "The Evidence for Bipolarons in Pyrrole Polymers", *Synthetic Metals*, 9:165–172 (1984).

Schwartz, M. A., "Transmembrane signalling by integrins", *Trends in Cell Biology*, 2:304–308 (1992).

Shinohara, H., et al., "Electrically stimulated rupture of cell membranes with a conducting polymer–coated electrode", *Bioelectrochemistry and Bioenergetics*, 22(1):23–35 (1989).

Singhvi, R., et al., "Engineering Cell Shape and Function", *Science*, 264:696–698 (1994).

Smith, A. B. and C. J. Knowles, "Investigation of the Relationship between Conductivity and Protein–Binding Properties of Polypyrrole", *Journal of Applied Polymer Science*, 43(2):399–403.

Street, G. B. and T. C. Clarke, "Conducting Polymers: A Review of Recent Work", *IBM J. Res. Develop.*, 25(1):51–57 (1981).

Street, G. B., "Polypyrrole From Powders to Plastics", *Handbook of Conducting Polymers*. New York: Marcel Dekker, 1:265–291.

Sudhakaran, P. R., et al., "Modulation of Protein Synthesis and Secretion by Substratum in Primary Cultures of Rat Hepatocytes", *Exp. Cell Res.* 167:505–516 (1986).

Swoboda, B. E. P. and V. Massey, "Purification and Properties of the Glucose Oxidase from *Aspergillus niger*", *The Journal of Biological Chemistry*, 240(5):2209–2215 (1965).

Trivedi, D. C. and S. K. Dhawan, "Investigations on the effect of 5–sulfosalicyclic acid on the properties of polyaniline", *Synth. Met.*, 58:309–324 (1993).

Tomomura, A., et al., "The Control of DNA Synthesis in Primary Cultures of Hepatocytes from Adult and Young Rats: Interactions of Extracellular Matrix Components, Epidermal Growth Factor, and the Cell Cycle", *J. Cell. Physiol.*, 130:221–227 (1987).

Umana, M. and J. Waller, "Protein–Modified Electrodes. The Glucose Oxidase/Polypyrrole System", *Anal. Chem.*, 58(14):2979–2983 (1986).

Vacanti, J. P., "Beyond Transplantation", *Arch. Surg.*, 123:545–549 (1988).

Vacanti, J. P., et al., "Selective Cell Transplantation Using Bioabsorbable Artificial Polymers as Matrices", *Journal of Pediatric Surgery*, 23(1):3–9 (1988).

Valentini, R. F., et al., "Polymer electret guidance channels enhance peripheral nerve regeneration in mice", *Brain Research*, 480(1/2):300–304 (1989).

Van der Pauw, L. J., "A Method of Measuring Specific Resistivity and Hall Effect of Discs of Arbitrary Shape", *Phillips Research Reports*, 13(1):1–9 (1958).

Wallace G. G. and Y. P. Lin, "Preparation and Application of Conducting Polymers containing Chemically Active Counterions for Analytical Purposes", *J. Electroanal. Chem.*, 247(1/2):145–156 (1988).

Wernet, W. and G. Wegner, "Electrochemistry of thin polypyrrole films", *Makromol. Chem.*, 188:1465–1475 (1987).

Wong, J. Y., et al., "Cell Attachment and Protein Adsorption to Polypyrrole Thin Films", *Mat. Res. Soc., Symp. Proc.*, 293:179–184 (1993).

Wong, J. Y., et al., "Cell Interactions with Fibronectin–Coated Electrically Conducting Polypyrrole Thin Films", *MRS Proceedings*, (Dec. 1993).

Wong, J. Y., et al., "Characterization of Electrically Conducting Polypyrrole Thin Films for Protein Adsorption and Cell Attachment", *Polymer Preprints*, 34(2):60–61 (1993).

Wong, J. Y., et al., "Electrically conducting polymers can noninvasively control the shape and growth of mammalian cells", *Proc. Natl. Acad. Sci. USA*, 91:3201–3204 (1994).

Yang, C. Y., et al., Morphology of Polyaniline in Solution Processed Blends with Poly(methyl methacrylate), *Polymer Preprints*, 34(1):790–791 (Mar. 1993).

Yang, S. and E. Ruckenstein, "Processable conductive composites of polyaniline/poly(alkyl methacrylate) prepared via an emulsion method", *Synth. Met.*, 59:1–12 (1993).

Yaoita, M., et al., "Electrically Regulated Cellular Morphological and Cytoskeletal Changes on an Optically Transparent Electrode", *Expl. Cell Biol.*, 57:43–51 (1989).

Zhou, Q. X., et al., "The Incorporation of Electrolyte Cations into Polypyrrole and Poly–3–Methylthiophene during Electrochemical Reduction", *J. Electroanal. Chem.*, 223:283–286 (1987).

% Adsorption of FN to various substrates at 1, 10, 100, and 1000 ng/cm² coating densities. (▦ PPy from chemical method; ▨ PPy from electrochemical method; ☐ petri dish; ☐ tissue culture dish; ◩ ITO)

FIG. 3

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 7 amino acid residues
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL: NO     ( i v ) ANTI-SENSE: NO     ( x i ) SEQUENCE DESCRIPTION: SEQ ID NO:1:

Leu  Ile  Gly  Arg  Lys  Lys  Thr
                          5

( 2 ) INFORMATION FOR SEQ ID NO:2:

( i ) SEQUENCE CHARACTERISTICS:
        ( A ) LENGTH: 5 amino acid residues
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL: NO     ( i v ) ANTI-SENSE: NO     ( x i ) SEQUENCE DESCRIPTION: SEQ ID NO:2:

Tyr  Ile  Gly  Ser  Arg
                  5

METHOD FOR ALTERING THE DIFFERENTIATION OF ANCHORAGE DEPENDENT CELLS ON AN ELECTRICALLY CONDUCTING POLYMER

The United States government may have certain rights in this invention by virtue of a National Science Foundation Grant No. BCS-9202311.

BACKGROUND OF THE INVENTION

The present invention is in the field of cell culture, and more specifically relates to a method of controlling cell function, proliferation, and differentiation by culturing cells on electrically conducting polymeric surfaces.

Initial studies on mammalian cell culture were disappointing. Many types of specialized cells plated on standard tissue culture plastic dishes dedifferentiated, lost function, and failed to proliferate. Studies have been conducted for a number of years to improve the viability, proliferation and differentiated function of eukaryotic cells cultured in vitro.

In an effort to improve the results obtained by plating cells in plastic dishes, Reid, L. M., et al. Long-term Cultures of Normal Rat Hepatocytes on Liver Biomatrix Ann. N.Y. Acad. Sci. (1980), reported that hepatocytes cultured on complex extracellular matrix substrates (ECM), prepared by extracting tissue to yield insoluble matrix, retained greater function. These results led to the use of gels of heterogenous basement membrane materials, such as Engelbreth-Holm-Swarm (EHS) mouse tumor derived laminin rich gels, reported by Li, et al., *Proc. Natl. Acad. Sci.* 84:136–140 (1987), and Matrigel™, as reported by Ben Ze'ev, et al., *Proc.Natl.Acad.Sci. USA* 85:2161–2165 (1988).

Subsequent studies using a purified basement membrane-like matrix as the culture substrate, reported by Bissell and Choun, *Scand. J. Gastroenterol.* 23:1–7 (1988), led to the conclusion that "[s]ustained expression of liver-specific function by hepatocytes in culture requires a basement membrane-like matrix as the culture substratum". Other investigators have found that cell growth and function varies depending on the presence or absence of specific extracellular matrix molecules. Sudhakaran, P. R., et al., *Exp. Cell Res.* 167:505–516 (1986); Sawada, et al., *In Vitro Cell Dev. Bio.* 23(4):267–273 (1987); Tomomura, A., et al., *J. Cell. Physiol.* 130:221–227 (1987); Jauregui, H. O., et al., *In Vitro Cell Dev. Biol.* 22:13–22 (1986).

It has also been reported that it is possible to exert control over growth by altering the composition or three dimensional configuration of polymeric attachment substrata, as reported by Kleinman, H. K., et al., *Anal. Biochem.* 166, 1–13 (1987). Bissel, D. M., et al., *J. Clin. Invest.* 79, 801–812 (1987); Michalopoulos, G., et al., *Exp. Cell Res.* 94, 70–78 (1975). One possible explanation for these effects is the existence of a general correlation between the shape of a cell, which is determined by the attachment substrate, and its function.

Matrix proteins alter cell behavior as a result of specific binding interaction with distinct types of cell surface ECM-receptors, such as the integrin family of receptors. However, ECM molecules cannot transmit growth and pattern-regulating signals based solely upon occupancy of cell surface ECM-receptors since the biological effects of matrix components vary greatly depending upon their structural configuration and density. Ingber, D. E. *Proc. Natl. Acad. Sci. USA*, 87, 3579–3583 (1990); R. Singhvi, et al., *Science*, 264:696–698 (1994). Cell shape is determined through the action of tensile forces that are generated within the intracellular cytoskeleton and resisted by ECM attachment points (Michalopoulos, et al., (1975); Harris, et al., *Science* (Wash. D.C.) 208:177–179 (1980); Ingber and Jamieson, *Gene Expression During Normal and Malignant Differentiation* L. C. Andersson, et al., editors, pp. 13–32 (Academic Press, Orlando, Fla. 1985)). Thus, one of the major effects of altering ECM structural integrity and is induction of cell shape changes: rigid dishes support cell extension whereas malleable substrata promote rounding. Endothelial cells also take on different forms on rigid dishes depending on the type of ECM molecules used for cell attachment (Ingber, et al., *In Vitro Cell Dev. Biol.* 23:387–394 (1987)).

Vacanti, et al., *Arch. Surg.* 123, 545–549 (1983), and Langer, et al., *J. Ped. Surg.* 23(1), 3–9 (1988), have reported that cells can be cultured in vitro and implanted, with subsequent proliferation and differentiated function, for several types of organ cells, based on the use of biocompatible matrices on which the cells are spaced apart enough to allow adequate diffusion of nutrients and gases to each of the cells to support viability.

However, there remains a significant need to provide a mechanism for controlling cell migration, growth and proliferation, both in vitro and in vivo, which would allow in vitro culturing of normal cells over a prolonged period of time and manipulation of in vivo proliferation, differentiation and function of cells on synthetic substrates.

It is therefore an object of the present invention to provide methods and compositions for controlling and manipulating the proliferation and differentiated function of cells in culture.

It is another object of the present invention to provide a method and compositions enhancing growth, proliferation and function of cells when implanted in vivo on artificial substrates and prostheses.

It is a further object of the present invention to provide a method and compositions for enhancing and controlling migration, growth and function of cells in vivo to repair tissue and bone damage, to remodel and construct tissue and to replace lost organ function.

SUMMARY OF THE INVENTION

Described are methods and cell culture or support systems for modifying the proliferation, differentiation, or function of anchorage dependent cells. Substrates are prepared which are formed of or coated with an electrically conducting biocompatible polymer which are used in vitro for cell culture, or in vivo to aid in healing, prevent surgical adhesions, repair bone or tissue defects, or replace missing or insufficient cellular function. Adhesion of the cells can be enhanced, and the effect on function, differentiation and proliferation modified, through binding of attachment molecules of defined types and in specific densities, to the conducting polymers. The cells are seeded onto, or the device implanted adjacent to, cells which are to be affected. Voltage is applied to the polymer in a range which induces the desired effect on the cells while not damaging the cells.

Examples demonstrate the effect of culturing two different types of cells on conducting polymer substrates and the effect of applied voltage and the modifications possible through variation of attachment molecule density on the conducting polymer substrate.

DETAILED DESCRIPTION OF THE INVENTION

Described is a method and cell culture system for altering the proliferation, differentiation, or function of anchorage dependent cells which includes associating the cells by either abutment or attachment with a surface formed of an electrically conducting polymer and applying an effective voltage to change the oxidation state of the polymer without damaging the cells.

The study of interactions of cells and proteins with chemical surfaces is important since most mammalian cells are anchorage-dependent and must attach to a surface in order to grow and proliferate. Surfaces formed of electrically conducting polymers are advantageous in that their properties, e.g., surface charge, wettability, conformational and dimensional changes, can be altered reversibly by oxidation or reduction. It has been shown that surface charge density and substrate wettability affect nerve regeneration (Valentini, R. F.; Sabatini, A. M.; Dario, P.; Aebischer, P. *Brain Res.*, 480 300– 304) (1989), protein adsorption and cell adhesion (Baier, R. E.; Shafrin, E. G.; Zisman, W. A. *Science*, 162, 1360–1368 (1968); Grinnell, F. *Int. Rev. Cytol.*, 53, 65–144) (1978). Furthermore, the shape of a cell has been shown to dictate its function: differentiated when rounded and growing when extended. Ingber, D. E. *Proc. Natl. Acad. Sci. USA*, 87, 3579–3583 (1990); Mooney, D., et al. *Cell. Physiol.*, 151, 497–505 (1992); Folkman, J.; Moscona, A. *Nature*, 273, 345–349 (1978).

It has now been determined that the function, proliferation, and differentiation of cells attached to or in proximity with electrically-conducting polymers can be manipulated through changes in the oxidation states of the polymers. The polymers are applied as coatings to substrates or used to form polymeric compositions to which the cells are attached, either directly or via attachment molecules, and cultured, either in vitro or in vivo. The amount of voltage (voltage×time of application) applied to the polymer determines the effect on the cells. Differentiation, proliferation and alteration in function (measured, for example, by protein production or DNA synthesis) is dependent on culture conditions, cell type, and substrate including both the polymer and type and density of any attachment molecules on the polymer.

I. Electrically Conductive Polymers.

Conjugated polymers represent a relatively new class of materials whose electrical and optical properties can be controllably varied over an extremely wide range, oftentimes in a completely reversible manner. This is typically accomplished either by chemical or electrochemical oxidation of the π-system of the polymer backbone or, in some cases, by direct protonation of the polymer backbone. Through this chemical "doping" process, it is possible to systematically vary the electrical conductivity of these materials from the insulating state to the conducting state. The electrically conductive forms of these materials are best described as p-type doped polymeric charge transfer salts in which the conjugated polymer supports positive charges that are delocalized over relatively short segments of the backbone, for example, over three to four repeating units for a highly oxidized polymer. Charge neutrality is maintained by a negatively charged counterion, which is usually derived from the doping agent.

The positively charged defect states created on the polymer backbone by the doping process can exist in many different forms, including as polarons (coupled radical cations), bipolarons (coupled dications) and solitons (noninteracting cations). Such charged defect states are believed to be the primary charge carriers in these materials and are therefore responsible for their electrically conductive nature.

Conducting polymers can be in the form of conjugated polyions or nonderivatized conjugated polymers. Nonderivatized conjugated polymers, i.e., those that do not include ionizable sidegroups, are significantly more environmentally stable than their derivatized polyion counterparts and also have been found to exhibit much higher electrical conductivities. Examples include conducting polymers such as polyaniline, polypyrrole and the poly(3-alkylthiophenes). These polymers exhibit significantly better environmental stabilities and much higher electrical conductivities than similar materials modified to contain ionizable sidegroups such as sulfonated polyaniline and poly(thiophene acetic acid).

Examples of nonderivatized conjugated polymers can be found in "*Conjugated Polymeric Materials: Opportunities in Electronics, Optoelectronics, and Molecular Engineering*", J. L. Bredas and B. Silbey, Eds., Kluwer, Dordrecht, 1991.

An electrically conducting polymer is a conjugated polymer which can be reversibly oxidized and reduced. Representative electrically conducting polymers include polyacetylene, polyaniline, polypyrrole, polythiophene, poly(phenylenesulfide), and poly(phenylenevinylene), among many others. Kanatzidis, M. G. *Chem, Eng. News*, 68, 36–54 (1990). Street, G. B.; Clarke, T. C. *IBM J. Res. Develop.*, 25, 51–57 (1981). Polymers can be deposited as coatings onto substrates or polymerized to form objects. Polymers can be applied as a single layer coating of a single polymer or as a multilayered film to alter the properties of the applied polymers.

Preparation of Polymer Coatings or Materials

The methods of synthesis and application for polypyrrole are typical of those for other electrically conducting polymers. Polypyrrole is perhaps the most widely studied electrically conducting polymer due to its chemical and thermal stability, ease of preparation, and electroactivity. Street, G. B. in *Handbook of Conducting Polymers*; Skotheim, T. A.; Marcel Dekker, Inc., New York, 1986; pp 265. Polypyrrole has been used in biological environments as biosensors (Umana, M.; Waller, J. *Anal. Chem.*, 58, 2979–2983) (1986); electrodes to obtain electrochemically controlled drug release (Miller, L. L. *Mol. Cryst. Liq. Cryst.*, 160, 297) (1988); as substrates which bind proteins (Prezyna, L. A.; Qiu, Y. J.; Reynolds, J. R.; Wnek, G. E. *Macromolecules*, 24, 5283–5287 (1991); Smith, A. B.; Knowles, C. J. *J. Appl. Polym. Sci.*, 43, 399–403 (1991); Wallace, G. G.; Lin, Y. P. *J. Electroanal. Chem.*, 247, 145–156 (1988)) and DNA. Minehan, D. S.; Marx, K. A.; Tripathy, S. K. *Polym. Mat.*

*Sci. Eng.*, 64, 341–2 (1991); and to burst cells associated with the polymer M. Yaoita, et al., *Exptl. Cell Biol.*, 57:43–51 (1989); H. Shinohar, et al., *Bioelectrochemistry and Bioenergetics*, 22:23–35 (1989), a section of *J. Electroanal. Chem.*, vol. 276 (Elsevier Sequoia S. A. Lausanne, Netherlands 1989).

Pyrrole can be either chemically or electrochemically polymerized to form polypyrrole. The chemical synthesis of polypyrrole in aqueous solution can be carried out by the method of S. P. Armes, *Synth. Met.*, 20, p. 365 (1987) and A. B. Smith and C. J. Knowles, *J. Appl. Polym. Sci.*, pp. 399–403, vol. 43, No. 2, Jul. 20, 1991. Briefly, anhydrous ferric chloride, e.g., 36 g., is dissolved in 400 mL double distilled water and cooled to 0° in an ice bath. Distilled pyrrole, (4 mL), precooled to 0° C., is added to the solution of ferric chloride with vigorous stirring for at least 2 hours. The insoluble polymer that forms is filtered on Whatman No. 6 filter membrane (Whatman Inc., Clifton, N.J. 07014) and washed extensively with water until a clear solution is obtained. It is further rinsed with ethanol and finally with diethyl ether before overnight drying at 35° C.

Chemical synthesis of polypyrrole in organic solvent can be carried out by the method of R. E. Myers, *J. Electron. Mater.*, 15, p. 61 (1986), and A. B. Smith and C. J. Knowles. Diethyl ether (300 mL) is added to 19.6 g of anhydrous ferric chloride contained in a 500 mL beaker. Cold distilled pyrrole (2.1 mL) is added to the stirred ferric chloride/ether solution precooled to 0° C. and stirred at this temperature for at least 1 hour. The insoluble product is recovered, washed and dried as described above.

Electrochemical synthesis of polypyrrole films can be carried out, for example, by the electrooxidation of pyrrole in a one-compartment cell equipped with a platinum working electrode, gold wire counter electrode, and a sodium chloride calomel reference electrode. In a typical preparation, an acetonitrile solution containing 0.1M tetraethylammonium tetrafluoroborate plus about 0.02M pyrrole is employed. Diaz, A. F.; Kanazawa, K. K. *Extended Linear Chain Compounds*; Plenum Press: New York, 1983 pp. 417–441. The oxygen in the solution is swept out with an inert gas prior to the electrolysis. In practice, a wide variety of solvents and electrolytes can be used as long as the electrical resistance of the solution is not high and the nucleophilicity does not interfere with the polymerization reaction.

Preparation of Multilayer Films

There are five principal methods for the preparation of ultrathin multilayered films: solution casting, Langmuir-Blodgett technique, chemisorption, the method of Decher, et al., and the method of Rubner, et al. Solution casting of preformed bilayer aggregates and annealing of spin coated films of copolymers yields layered structures, although alignment of the layers and the positioning of molecules with respect to each other is limited. In the Langmuir-Blodgett (LB) technique, a film is prepared on the surface of water and then transferred onto solid substrates. This method, however, is generally only applicable to flat substrates. Another method is based on chemisorption.

Decher, et al., *Thin Solid Films* 210/211, 831 (1992) and DE 4026978 (WO92-073188/10), have demonstrated that it is possible to build up multilayer thin films of polymers onto charged surfaces via the alternating deposition of polycations and polyanions. The basis for this multilayer assembly process is the ionic attraction of the permanently fixed charges that exist on the polycations (positive charge) and polyanions (negative charge). In essence, the excess charge of a polyion adsorbed onto a substrate surface is used to attract a polyion of the opposite charge onto the surface. Multilayer thin films are fabricated by simply alternating the dipping process.

This approach can be used to manipulate a variety of different polyions, including conjugated polyions (conjugated polymers fitted with ionizable sidegroups), which function as conducting polymers. However, the addition of ionizable sidegroups to the repeat structure of a conjugated polymer can compromise the level of conductivity achievable with the polymer. It is therefore more desirable and useful to be able to fabricate more conventional conjugated polymers such as polyaniline and polypyrrole into ultrathin multilayer thin films.

Milliken Corp. has disclosed a procedure for coating various textile fibers with uniform, electrically conductive films of polypyrrole and polyaniline. Specifically, the deposition of an electrically conductive coating of polypyrrole onto the fibers is accomplished by placing the fibers into a dilute aqueous solution of pyrrole that also contains an oxidizing agent such as ferric chloride and negative counterions suitable for enhancing the conductivity and conductivity stability of the polymer. The counterions are typically added in the form of sulfonic acids such as naphthalene disulfonic acid. A typical coating solution contains about 10 g/l ferric chloride anhydride, 5 g/l toluenesulfonic acid and 0.2 g of pyrrole monomer.

A very versatile means for fabricating multilayer thin films with new electrical and optical properties is disclosed by Rubner, et al., in PCT/US94/07182 by Massachusetts Institutes of Technology, which utilizes a molecular-level, layer-by-layer deposition process. This process is especially useful for the construction of heterostructure thin films with complex molecular architectures and thicknesses that are controllable at the molecular level. The basic process used to create alternating layer thin films involves dipping a substrate into a dilute solution of a p-type doped polymer such as a p-doped conjugated polymer, rinsing the substrate with water (or other solvent for the polymer) and then dipping it into a dilute solution containing a polyanion or a water soluble, non-ionic polymer. This process can be repeated as many times as desired to build multilayer thin films in which each bilayer deposited is only about 10–100 Å in thickness, depending on parameters such as solution concentration, doping level, pH, and ionic strength.

The generation of water soluble, p-type doped conducting polymers can be accomplished in a number of different ways. In one embodiment, conducting polymer chains are formed in situ in a dilute aqueous solution primarily consisting of a monomer and an oxidizing agent. In this case, the conducting polymer is actually created in the solution and subsequently spontaneously adsorbed onto the substrate surface as a uniform, ultra-thin film of between approximately 10 to greater than 250 Å in thickness, more preferably between 10 and 100 Å.

Thin, electrically conductive coatings of polypyrrole and polyaniline, for example, can be formed on various substrates by simply placing the object to be coated in an aqueous bath containing dilute (less than about 0.1 m/l) quantities of pyrrole (or aniline) monomer and a suitable oxidizing agent such as ferric chloride or ammonium peroxysulfate. The use of dilute solutions of the monomer insures that the electrically conductive polymer formed from the oxidative polymerization of the monomer will be deposited exclusively onto the substrate to be coated as opposed to simply polymerizing in the solution and precipitating out as an insoluble powder.

Highly uniform and dense multilayer thin films can be easily fabricated by simply dipping the substrate into a dilute aqueous solution of a polyanion, whereby a monolayer of this material is deposited onto the p-type doped conducting polymer. This process of alternately depositing layers of a p-type doped polymer and a negatively charged polyanion can be repeated as often as needed to create thin films with precisely controlled thickness and structure.

Alternatively, in a second embodiment, preformed conducting polymers are used directly by forming dilute solutions of their doped forms in suitable solvent systems. In this case, it is necessary to control the type of solvent system used and the level and type of chemical doping of the polymer chains. The general procedure involves first dissolving the undoped polymer in a suitable organic solvent and subsequently diluting this polymer solution with a solvent that contains a dopant for the polymer. This produces a solvent system capable of solvating the doped polymer chains. In the case of polyaniline, for example, it has been found that dilute aqueous solutions can be easily formed by first dissolving the nonconducting emeraldine-base form of this polymer in dimethylacetamide (DMAc) (or n-methyl pyyrolidone) (NMP) and subsequently diluting this solution with acidic water such that the final solution has a 90/10 water to DMAc volume ratio. Since the final step of this process also acid dopes the polymer, the level of doping can be easily adjusted by controlling the pH level of the final dipping solution. Solutions with polyaniline concentrations as high as 0.01 m/l are easily prepared with this procedure. The net result is a stable, water based solution (90% water) of doped polyaniline that is quite well suited for molecular self-assembly via alternate deposition with polyanions.

Polyaniline (PAn) presents itself as well suited for a variety of applications due to its relative ease of synthesis, low cost, and stable electrical conductivity. The achievable levels of conductivity, ranging from completely insulating up to about 200 S/cm, are generally quite adequate for a wide variety of applications calling for electronic conduction. Early work has shown PAn to have quite limited processability due to its very high melting temperature, and limited solubility. Only the base form of PAn (nonconducting) was considered soluble, primarily in NMP, DMAc and dimethylsulfoxide (DMSO), but not in common solvents. Once doped by either protonation or by oxidation, the resulting conducting form generally became intractable.

Several research groups have reported approaches to process doped PAn; both homopolymer films, as well as conducting blends. For example, the use of "functionalized" protonic acids, primarily large sulfonic acids as PAn dopants, renders the doped polymer soluble in several organic solvents [C. Y. Yang, et al., *Polymer Preprints*, ACS Meeting, Denver, March 1993; Y. Cao and A. J. Heeger, *Synth. Met.*, 52, 193 (1992); Y. Cao, P. Smith and A. J. Heeger, *Synth. Met.*, 48 (1992), 91; A. Andreatta and P. Smith, *Synth. Met.*, 55, 1017 (1993)]. Blends with several host polymers have been reported, including polymethylmethacrylate (PMMA), nylon, polyvinylchloride (PVC), polystyrene (PS), polyvinyl acetate (PVA), polypropylene, polyethylene (PE), ABS, and polycarbonate [Y. Cao, P. Smith and A. J. Heeger, *Synth. Met.*, 48, 91 (1992); A. Andreatta and P. Smith, *Synth. Met.*, 55, 1017 (1993)]. Conducting PAn/poly (alkyl methacrylate) blends have been prepared by emulsion polymerization in the presence of HCl [S. Y. Yang and E. Ruckenstein, *Synth. Met.*, 59 (1993)]. Conducting PAn films have been cast from a ferric chloride solution in nitromethane, starting with either PAn base or already-doped PAn, as described by U.S. Pat. No. 4,983,322 to Elsenbaumer. Doped PAn can also be solubilized by the addition of a Lewis base which acts to complex the dopant, rendering the PAn soluble, as described in International Patent Application, No. W092/11644 by Han, et al., (1992). PAn doped with 5-sulfosalicylic acid (SSA) is soluble in DMSO, dimethylformamide (DMF), and NMP, as reported by D. C. Trivedi and S. K. Dhawan, *Synth. Met.*, 58, 309 (1993). Two groups have reported doping PAn with a polymeric dopant, sulfonated polystyrene: Y.-H. Liao and K. Levon, *PSME Preprints*, ACS Meeting, Chicago, August 1993; and B. D. Malhotra, et al., *J. Appl. Polym. Sci.*, 40, 1049 (1990).

II. Substrates and Polymeric compositions.

In general, the electrically conducting polymer must be applied to the surface to which the cells attach, or abut, in the case of tissue into which the material is implanted, in order to be useful. The polymer can either be used as a coating on the surface of another material or to form the material itself.

There are two basic types of materials onto which the attachment molecules are placed for controlling migration, growth and proliferation of the cells to be cultured. One class includes biocompatible materials which are not biodegradable, such as poly(styrene), poly(ethylene vinyl acetate), poly(propylene), poly(methacrylate), poly (ethylene), poly(ethylene oxide), glass, polysilicates, poly (carbonates), teflon, fluorocarbons, nylon, and silicon rubber. The other class of materials includes biocompatible, biodegradable materials such as poly(anhydrides), poly (glycolic acid), poly(lactic acid), poly(orthoesters), poly (propylfumerate), proteins and polymerized proteins such as collagen, and polysaccharides and polymerized polysaccharides, such as glycosaminoglycans, and combinations thereof.

In vitro Culture

For in vitro culture, the polymer can be applied as a coating to culture flasks, wells, or roller bottles, which serve as culture containers. Alternatively, the polymer can be applied as a coating to, or polymerized to form, microcarrier beads. Microcarrier beads are commercially available from suppliers such as Sigma Chemical Co., St. Louis, Mo., and Pharmacia Fine Chemicals, Piscataway, N.J., as dextran-based beads, glass microcarrier beads (90–150 micron and 150–210 micron diameters). In the preferred embodiment, any coating on the bead such as gelatin would be removed, the bead would be coated with conducting polymer, and the gelatin or other attachment molecules or "adhesion enhancers" (such as albumin) reapplied to the conducting polymer coating, for example, in the case of gelatin, in the same densities as provided by Sigma, i.e., 1.02 to 1.04 g/cm$^3$. Typically, the culture containers are formed of plastics such as polystyrene, polypropylene, and polyterepthalate, on which the conducting polymer can be routinely applied, or as described above, even prepared as a blend with the electrically conducting polymers.

In vivo culture

Scaffolds for tissue engineering (implantable matrices) can be coated with, or made of, conducting polymers to enhance proliferation, growth or function of implanted cells or cells which migrate into, attach and proliferate within the implanted matrices. Other materials for implantation include sutures, bone screws, nails and plates, tubes and sheets, vascular stents, adhesion prevention devices (typically films, polymeric coatings applied as liquids which are polymerized in situ, or other physical barriers), and wound healing products (which vary according to the wound to be healed from films and coating to support structures). These are particularly useful in tissue repair or reconstruction, particularly reconstruction of vessels, diaphragms, bone repair, and for implantation of cells, both normal and genetically engineered, to replace lost function. L. S. Lavine, et al., *J. of Bone and Joint Surgery*, 625–630 (1987), a general review of electrical stimulation for repair of bone, describes a number of devices which can be modified for use with electrically conducting polymers.

As described by Langer, et al., *J. Ped. Surg.* 23(1), 3–9 (1988), W088/03785 and EPA 88900726.6 by Massachusetts Institute of Technology, a matrix for implantation to form new tissue should be a pliable, non-toxic, porous template for vascular ingrowth. The pores should allow vascular ingrowth and the seeding of cells without damage to the cells or patient. These are generally interconnected pores in the range of between approximately 100 and 300 microns. The matrix should be shaped to maximize surface area, to allow adequate diffusion of nutrients and growth factors to the cells and to allow the ingrowth of new blood vessels and connective tissue. In the preferred embodiment, the matrix is formed of a bioabsorbable, or biodegradable, synthetic polymer such as a polyanhydride, polyorthoester, or polyhydroxy acid such as polylactic acid, polyglycolic acid, and copolymers or blends thereof. Non-degradable materials can also be used to form the matrix. Examples of suitable materials include ethylene vinyl acetate, derivatives of polyvinyl alcohol, teflon, nylon, polymethacrylate and silicon polymers. The preferred non-degradable materials are ethylene vinyl acetate meshes and polyvinyl alcohol sponges. A non-absorbable polyvinyl alcohol sponge is available commercially as Ivalon™, from Unipoint Industries. Collagen can also be used, but is not preferred.

These materials are all commercially available. All polymers for use in the matrix must meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy, with respect to toxicology by initial screening tests involving Ames assays and in vitro teratogenicity assays, and implantation studies in animals for immunogenicity, inflammation, release and degradation studies.

III. Attachment Molecules and Application to Polymer.

Attachment Molecules.

Attachment molecules are defined as any natural or synthetic molecule which is specifically bound by cell surface receptors. These include natural and synthetic molecules having one or more binding sites. Examples of natural molecules are extracellular matrix factors such as fibronectin and laminin. Examples of synthetic molecules are peptides containing the binding sites of fibronectin. In some embodiments, attachment of the cells to the polymer is enhanced by coating the polymers with compounds such as basement membrane components, gelatin, gum arabic, collagens types I, II, III, IV, and V, fibronectin, laminin, glycosaminoglycans, mixtures thereof, and other materials known to those skilled in the art of cell culture. Extracellular matrix molecules (ECM) include compounds such as laminin, fibronectin, thrombospondin, entactin, proteoglycans, glycosaminoglycans and collagen types I through XII. Other natural attachment molecules include simple carbohydrates, complex carbohydrates, asialoglycoproteins, lectins, growth factors, low density lipoproteins, heparin, poly-lysine, thrombin, vitronectin, and fibrinogen. Synthetic molecules include peptides made using conventional methods to incorporate one or more binding sites such as R G D from fibronectin, L I G R K K T (SEQ ID NO: 1) from fibronectin and Y I G S R (SEQ ID NO: 2) from laminin.

Application of Attachment Molecules

Methods for applying attachment molecules to substrates are known. There are four principle methods that have been utilized: attachment of molecules to substrate by applying attachment molecules in a solution such as PBS or a high pH, carbonate buffer and adsorption of the molecules to the substrate surface; ionic binding of attachment molecules to substrate; covalent binding of molecules to the substrate surface by chemical reactions using reagents such as glutaraldehyde or carbodiimide; and drying of attachment molecules on the substrate surface.

As referred to herein, the concentration of attachment molecules producing a specific effect is measured in units of attachment molecules per unit of available substrate surface area. In general, when molecules are applied to a substrate such as polystyrene, approximately 60 to 80% of these molecules will be bound when added at high concentrations; approximately 80 to 95% of these molecules will be bound when added at low concentrations, when a procedure such as the high pH carbonate coating solution containing attachment molecules is applied to a substrate. Efficiencies are lower for procedures when the substrate is not highly reactive. For example, as measured using $^{125}$-I labelled type I collagen applied to a three dimensional poly(glycolic acid) matrix (PGA), 20 to 40% of collagen molecules were adsorbed from a carbonate solution and 40 to 50% of collagen molecules were bound by air drying collagen onto the PGA.

In one method for applying attachment molecules to substrate, defined densities of purified attachment molecules are placed onto artificial matrices by preincubating the matrices for 24 hours at 4° C. with a pH 9.4 carbonate buffer (15 mM sodium carbonate, 35 mM sodium bicarbonate) containing different concentrations of the attachment molecule. Non-adsorbed molecules are washed free from the matrix prior to use (e.g., cell plating). In another method, adsorption of attachment molecules or other attachment moieties is accomplished using solvents such as phosphate or Hanks-buffered saline, media, acetic acid with ammonium hydroxide vapor neutralization, or organic solvents. In a third method, molecules are dried directly onto the surface of the matrix. In a fourth method, defined densities of attachment molecules are placed on the matrix by chemically cross-linking to reactive side groups present within the matrix. For example, synthetic RGD peptides may be chemically cross-linked to a matrix that contains free amino or carboxyl groups using glutaraldehyde (2% glutaraldehyde by volume in a buffered solution, for example, 0.1M sodium cacodylate, pH 7.4) or carbodiimides as cross-linker agents. In this method, aqueous solutions containing varying concentrations of purified attachment molecules or other attachment moieties are incubated with the artificial matrices in the presence of a constant amount of glutaraldehyde or carbodiimide.

Appropriate conversions must be made when using small synthetic peptides composed almost entirely of individual binding sites or polymers having multiple binding sites to yield an equivalent density of binding sites. In general, maximal stimulation of DNA synthesis and cell proliferation is achieved when greater than when approximately 5000 molecules (based on fibronectin) are bound per $\mu m^2$ of surface. In general, cell differentiation is promoted at densities less than approximately 5000 molecules/$\mu m^2$. An example of a commercially available synthetic peptide containing a binding site is "Peptite™ 2000", a commercially available form of RGD peptide from Telios Pharmaceuticals that coats onto dishes from phosphate-buffered saline when incubated 24 h at 4° C.

Defined densities of attachment molecules have been divided into two ranges based on studies with certain cell types: between 0.001 ng attachment molecule/cm$^2$ and up to 500 ng attachment molecule/cm$^2$, and between greater than 500 ng attachment molecule/cm$^2$ and 500 $\mu$g/cm$^2$. Cells tend to be more rounded, differentiated and functional at the lower range. Cells tend to migrate more, be more spread out in appearance, synthesize DNA and proliferate at the higher range. Defined densities can be applied as a gradient to achieve more than one effect on the same substrate, i.e., migration and proliferation initially, then differentiation and functioning. Cells can also be cultured on a substrate having attachment molecules at one concentration, then moved to, or overlaid with, substrate having attachment molecules in another concentration.

IV. Attachment and Culture of Cells

In vitro Cell culture

Cells from mammalian tissues or lower animals, plant cells, transformed cells, genetically-engineered cells, or any other cells that remain functional when attached or abutted to a substrate can be cultured on the electrically conducting polymers as described herein for controlling proliferation (i.e., migration and growth), differentiation and function on an electrically conductive substrate. Specific examples include endothelial cells, parenchymal cells such as hepatocytes, Islet cells, and other organ cells, muscle cells, nerve cells, cells such as osteoblasts and chondrocytes which form bone and cartilage, respectively, and other anchorage dependent mammalian and plant cells.

In general, the requirements for each type of cell as to growth versus differentiation and function will be specific as to cell type, as well as substrate and attachment molecule, and culture conditions including time and extent of applied voltage.

Cells, such as hepatocytes, may be obtained from whole organs after perfusion with collagenase or chelators or by mechanical dissociation. Cells can also be obtained from established cell lines that are maintained in culture. Cells can be manipulated genetically before or after culture on the attachment molecule-coated matrices. Cells can be genetically altered cell lines or cells which are transfected with genetic material after attachment to the molecules on the substrates. The efficiency of gene transfection may be increased using high attachment molecule densities that promote the highest rate of DNA synthesis and cell growth.

Differentiated cell functions expressed by cells cultured on electrically conductive substrates may be measured using specific, quantitative assays. For example, quantitative immunoblot assays can be used to measure secretion of liver-specific proteins, such as albumin, fibrinogen, and transferrin, by cultured hepatocytes. It is also possible to identify cell type by the cytokeratins present, and altered expression of cytokeratin genes has been related to growth in hyperplastic and neoplastic epithelial cells in culture. There are reports by Denk, Lackinger, *Sem. Liver Disease* 6(3), 199–211 (1986), that the intermediate filament composition of cultured hepatocytes differs from native liver, the presence of higher molecular weight cytokeratins is one of the steps in the carcinogenesis of the liver, as described by French, *Nature* 1(3), 217–231 (1981), and Meierhenry, et al., *Hepatology* 3(1), 90–95 (1983), and tubulin expression increases in regenerating liver. Other investigators have looked at the metabolic functions of hepatocytes. These methods include induction of tyrosine aminotransferase by corticosteroids, as reported by Landry, J., et al., *J. Cell Bio.* 101, 914–923, P-450 (1985) content of cultured cells, and monitoring capacity for glucogenesis. A bromosulfaphthalein uptake and secretion assay can also be used to measure hepatocytes' ability to take up, conjugate (metabolize), and secrete organic anions.

For cell functions that require DNA synthesis, such as cell proliferation and gene transfection, optimum conditions can be identified by measuring effects on cellular DNA synthesis using standard radioactive labelling (e.g., incorporation of tritiated-thymidine) or immunocytochemical (e.g., bromodeoxyuridine uptake) methods. Effects on cell growth may also be measured by quantitating increases of cell number during culture on matrices coated with different attachment molecule densities using a Coulter Counter or colorimetric cell counting assay (e.g., acid phosphatase assay).

Morphological techniques can also be used to assess optimum conditions. For example, cells are fixed in 1% glutaraldehyde, washed with PBS, dehydrated in methanol, air dried, and stained with Coumassie brilliant blue. Cell shapes (projected cell areas) are quantitated by computerized morphometric analysis using an Image I Processor (Image Technology Corporation). Eight random areas are chosen and the projected cell area for every cell in the field is measured; at least 25 cells are analyzed per experimental condition. Quantitative dot-blot assay can be used to determine secretion rates for the proteins albumin, transferrin, fibrinogen, and fibronectin from the cell cultures. Media samples from the cultures are serially diluted and loaded in duplicate onto nitrocellulose paper (0.1 micron pore size using a 96 well minifold apparatus, Schleicher-Schuell). Protein standards are also loaded in duplicate at decreasing levels from 300 to 10 ng/dot. The blot is then exposed to an appropriate primary antibody (rabbit anti-rat albumin and anti-rat transferrin from Cappel, and rabbit anti-rat fibrinogen from Sigma) for the protein being quantitated. The non-bound primary antibody is washed away after one hour, and the blot is exposed to donkey anti-rabbit IgG labelled with $^{125}$I (Amersham) for an additional hour. The non-bound secondary antibody is washed away, and an autoradiograph of the blot made using XOMAT-XAR5 film. The dots are then punched out and bound $^{125}$I measured using a gamma counter to determine the total amount of bound antibody. A calibration curve is generated by relating known amounts of standard protein to total count per minute bound. The linear portion of the standard curve is then used to quantitate the amount of protein in the unknown media samples. Secretion rates are normalized for cell number before the modulating effects of different attachment molecule densities are compared.

The pattern of protein secretion from cultured cells is determined by pulse labelling cultures from 46–48 hours post-attachment with $^{35}$S labelled methionine (ICN) in methionine free William's E media (Gibco). The media is collected after the two hour labelling, and equal amounts of protein are analyzed by sodium dodecyl sulfate-polyacrylamide gel electrophoresis (SDS-PAGE). Autoradiographs are prepared with XOMAT-XAR5 film.

DNA synthesis is used as a measure of potential for cellular proliferation. Cells are pulse labelled for 16 hours beginning at 48 hours post-cell attachment with $^3$H-thymidine, and subsequently fixed as outlined above. The dishes are coated with Kodak NTB2 autoradiography emulsion, and allowed to expose for seven days. Autoradiographic grains are developed using Kodak D-19 developer.

The percentage of cells actively synthesizing DNA is quantitated by choosing 8 random areas on each dish and counting those cells with nuclear grains versus the total number of cells. A minimum of 35 cells is counted per dish.

In vivo Cell Culture

In a manner similar to that described with reference to in vitro cell culture, it is readily ascertainable which polymers to apply to a coating or to form as an implant in order to achieve a desired effect on implanted cells. Cells may be seeded into and onto a matrix for implantation or they may migrate into and proliferate on and within the matrix or implant. Means for applying an electrical voltage are connected to the implant. This can be as simple as needles which are inserted to contact the implant or electrodes attached to the implant prior to implantation which are externally connected to an appropriate electrical source.

As noted above, applications for in vivo use include manipulating differentiation of cells either to increase production of specific proteins or decrease production of specific proteins, such as a particular hormone, or induce proliferation and growth, for example, to promote healing, especially following surgery or trauma to bone or soft tissues. Those skilled in the art can readily determine exactly how to use these materials and the conditions required using commercially available reagents without undue experimentation.

V. Application of Voltage to Polymers

It has been experimentally determined from in vitro studies such as those described in the examples, that the voltage range for changing the oxidation state of the polymers is between −0.25 and 0.1 V, versus Ag/AgCl. The voltage is typically applied for a period of time equivalent to one-half to five hours in vitro in a cell culture solution, pH 7.4.

The present invention will be further understood by reference to the following non-limiting examples.

The reproductive cycle of a typical eucaryotic cell can be divided into four phases, known as $G_1$ (gap 1), S (DNA synthesis), $G_2$ (gap 2), and M (mitosis). The beginning of S phase and the beginning of M phase are each signaled by soluble cytoplasmic factors, the S-phase activator and the M-phase-promoting factor, respectively.

In most cells the DNA in the nucleus is replicated during only a limited portion of interphase known as the S phase of the cell cycle. Between the end of the M phase and the beginning of DNA synthesis, there is usually an interval, known as the $G_1$ phase; a second interval, known as the $G_2$ phase, separates the end of DNA synthesis from the beginning of the next M phase. Interphase is thus composed of successive $G_1$, S, and $G_2$ phases, and it normally comprises 90% or more of the total cell-cycle time. For example, in rapidly proliferating cells of higher eucaryotes, M phases generally occur only once every 16 to 24 hours, and each M phase itself lasts only 1 to 2 hours.

A population of cells in culture will be distributed throughout all phases of the cell cycle at any one point in time, because of random variability in the rate of cycling of the individual cells. However, synchronous cell populations can be obtained in several ways. One of the oldest techniques is to expose the cells to a drug that interferes with a specific step in the cycle and stops cells from progressing beyond it: prolonged exposure causes all the cells to come to a halt at that same point, so that when the block is removed they resume cycling together in step. Excess thymidine is commonly used for this purpose. During a cell cycle, however, many processes are occurring in parallel, and one cannot assume that all of them will be halted by the drug in a well-coordinated way. For this reason it is better, where possible, to use methods of preparing synchronized cell populations that do not interfere with the cell's normal progress through the cycle. For many mammalian cells in culture, the simplest and best procedure takes advantage of cytoskeletal change that occurs in cells in M phase, causing the cells to "round up." The rounded M-phase cells adhere so weakly to the culture dish that they can be removed by gentle agitation. Mitotic cells collected by this technique of mitotic shake-off constitute a synchronous population that will almost immediately enter the $G_1$ phase of the cycle. Alternatively, because cells generally become progressively bigger as they proceed through the cycle, centrifugation can be used to select large numbers of cells at each stage of the cycle on the basis of their size. B. Alberts, et al., eds., *Molecular Biology of the Cell*, 2nd edition, pp. 727–738 (Garland Publishing Co., N.Y. 1989); L. Kleinsmith, et al., *Principles of Cell Biology*, pp. 490–491 (Harper & Row Publishers, Inc. N.Y. 1988). However, these techniques may involve trypsinization of the cells, which can damage them.

In many mammalian cells in culture a cytoskeletal change occurs in cells in M phase, causing the cells to "round up." However, it is important to note that cell spreading does not cause cells to proliferate, it only governs progression from $G_0$ to S phase. For example, migrating cells and cells blocked in $G_2$ can spread on FN-coated dishes without growing; however, cell shape is coupled to growth when cells become nonmotile and form focal adhesions during $G_1$ phase. D. Ingber, *Proc. Natl. Acad. Sci. USA*, 87, 3579–3583 (May 1990).

When cells are cultured on oxidized polypyrrole, cells attach and spread normally. However, as shown in the examples, when the polypyrrole is reduced, the cells round. This phenomenon is reversible. Therefore, the reduction of the polypyrrole substratum can be used to change the shape of the associated cells, and thus their position in the cell cycle.

EXAMPLE 1

Effect on Bovine Aortic Endothelial Cells of Reduction and Oxidation of Substratum of Fibronectin-Coated Polypyrrole.

(a) Optically-transparent thin films of polypyrrole were synthesized which were suitable for viewing under the inverted phase-contrast light microscope. The electrochemical method was used, since it allows easy control of film thickness. Thin films of polypyrrole were synthesized potentiostatically at 1.1 V (versus saturated calomel electrode) on an optically-transparent indium tin oxide (ITO) from a solution containing 0.1M pyrrole (purified on an activated alumina column) and 0.1M tosylate in acetonitrile with 0.05 v % ultrapure water. Diaz, A. F.; Kanazawa, K. K. *Extended Linear Chain Compounds*; Plenum Press: New York, 1983, pp. 417–441. In addition, the solution was degassed with Ar before each film deposition. Film thicknesses were on the order of 0.1 μm. Wernet, W., et al., *Makromol. Chem.*, 188, 1465–1475 (1987).

Figure 1:
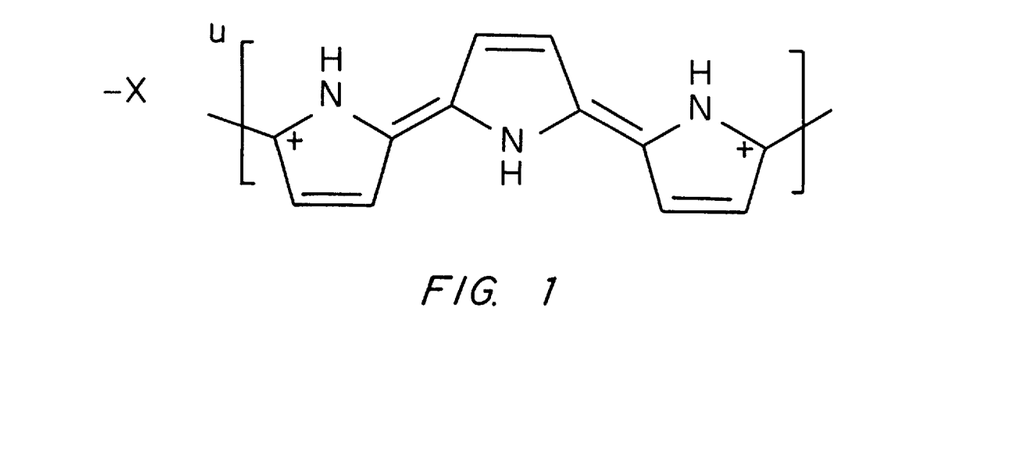
FIG. 1 shows the structure of polypyrrole in the oxidized state. X indicates a dopant anion.

Polypyrrole obtained via electrochemical synthesis exists in the oxidized state as a polycation with dopant anions to balance the charge (FIG. 1) and can be cycled between its oxidized and neutral forms electrochemically. The neutral form, however, is very unstable in air and water and spontaneously oxidizes after the reduction potential is removed. Li, Y.; Qian, R. *Synth. Met.*, 28, C127–C132 (1989). On the other hand, if the polymer is held at its reduction potential, it will remain in the neutral state. Since an experimental objective was to perform cell studies in biological media, the electrochemical and UV/VIS spectroelectrochemical properties of polypyrrole were evaluated in cell culture medium.

Serum-free conditions were chosen in order to produce a well-defined system. All substrates were pre-coated with 10 $\mu g/cm^2$ of fibronectin (FN) in 0.1M carbonate buffer, and the amount of protein adsorbed was quantitated using $I^{125}$-labeled fibronectin. Ingber, D. E. *Proc. Natl. Acad. Sci. USA*, 87, 3579–3583 (1990). FN is an extracellular matrix protein which mediates cell attachment and spreading. Grinnell, F. *Int. Rev. Cytol.*, 53, 65–144 (1978); Ingber, D. E. *Proc. Natl. Acad. Sci. USA*, 87, 3579–3583 (1990); Mooney, et al., *Cell. Physiol.*, 151, 497–505 (1992). The attachment to and spreading of bovine aortic endothelial (BAE) cells on thin films of polypyrrole was examined in both the oxidized and neutral states of the polymer.

Fibronectin-coated polypyrrole was able to be switched between its oxidized and neutral states in cell culture medium with reduction and oxidation potentials at –0.5 V and 0 V versus Ag/AgCl, respectively. A broad peak near 800 nm associated with the bipolarons (Scott, J. C.; Bredas, J. L.; Yakushi, K.; Pfluger, P.; Street, G. B. *Synth. Met.*, 9, 165–172 (1984)) was present in the UV/VIS absorption spectrum of the oxidized polymer. At –0.5 V (vs. Ag/AgCl), polypyrrole was switched to its neutral state, as followed by the disappearance of the peak near 800 nm and the appearance of a peak near 370 nm which has been shown to be characteristic of the neutral polymer. Genies, E. M.; Pernaut, J. M. *J. Electroanal Chem.*, 191, 111–126 (1985).

Cells attach and spread onto oxidized polypyrrole which is coated with FN, indicating that FN is able to mediate cell attachment and spreading when it adsorbs onto thin films of polypyrrole, as demonstrated by photomicrographs of Coomassie Brilliant blue-stained bovine aortic endothelial (BAE) cells after 4 hours culture on oxidized (a) or neutral (b) polypyrrole coated with fibronectin (FN). Cells remained rounded, however, when plated onto neutral polypyrrole. This effect was not a result of culturing the cells in an environment outside of the incubator, since cells attached and spread normally onto control FN-coated tissue culture, petri dish, and oxidized polypyrrole surfaces in the same experiment. In order to check that this effect was not due to electrochemical products being formed, cells were plated onto polypyrrole held at its oxidation potential (O V, vs. Ag/AgCl). These cells attached and spread after three hours, indicating that cells were remaining round on the surface due to some process occurring during the reduction of polypyrrole.

In order to further study the effect of reduction of the polypyrrole substrate on cell shape, the effect was studied of applying a reduction potential to FN-coated polypyrrole surfaces on which cells had been first allowed to attach and spread. After application of –0.25 V (vs. Ag/AgCl) for 1 hour, the pseudopods of the cells began to retract, and the cells became rounded. Cells were not being killed since the viability of the rounded cells was 84±5% (compared to 91±2% for spread cells on FN-coated petri dishes) as determined by the Live/Dead® Viability/Cytotoxicity assay (Molecular Probes Inc., Eugene, Oreg. 97402). As shown by the cyclic voltammogram during reduction, the cells are exposed only to a current density of 20 $\mu A/cin$, and a current density of a few $mA/cm^2$ was shown not to affect cell attachment, spreading and growth of fibroblasts. Giaever, I.; Keese, C. R. *Proc. Natl. Acad. Sci, USA*, 81, 3761–3764 (1984). In addition, when the same experiment was repeated on FN-coated gold or indium tin oxide (ITO) surfaces, cells did not round up after 1 hour application of –0.25 V (vs. Ag/AgCl). Thus, this effect most likely is not due to an electrical field. Furthermore, since (1) the conductivity of electrochemically reduced polypyrrole films are on the order of $10^{-6}$ $Scm^{-1}$ (Qian, R.; Qiu, *J. Polym. J.*, 19, 157–182 (1987)), compared to approximately 1 $Scm^{-1}$ for cell culture medium, and (2) the cells are not a confluent monolayer, the current generated is directed towards reducing the polymer film and not the cells.

In order to determine whether or not fibronectin was being released during reduction, the release of $I^{125}$-labeled fibronectin was examined. In the absence of cells, approximately the same amount of fibronectin was being released from wells in which the polypyrrole was being reduced compared to untreated wells.

(b) Synthesis of Polypyrrole. Pyrrole (Kodak, Rochester, N.Y.) was purified by passage through an activated alumina column until it became colorless. Electrochemical synthesis of polypyrrole (Diaz, A. P., et al., *J. Chem. Soc. Chem. Commun.* 14, 635–636 (1979)) was carried out in an electrochemical cell containing an optically transparent indium tin oxide anode (40 ohms per square; Delta Technologies, Stillwater, Minn.), a platinum mesh counter-electrode, and a saturated calomel reference electrode (SCE). The electrodeposition solution contained 0.1M tetraethylammonium p-toluenesulfonate (Alfa Products, Ward Hill, Mass.) in acetonitrile with 0.5% (vol/vol) ultrapure water (Milli-Q Reagent Water System; Millipore). Films were made potentiostatically at 1.1 V (versus SCE; Pine Instruments AFRDE4 bipotentiostat; Linseis x-y recorder) until about 100 $mC/cm^2$ was passed. J. Y. Wong, et al., *PNAS*, 91:3201–3204 (1994).

Polymer Characterization. Cyclic voltammetry experiments were carried out with a Pine Instruments AFRDE4 bipotentiostat and Linseis x-y recorder. The polypyrrole films were cycled between +0.4 and –1.0 V at 50 mV/sec in serum-free medium [Dulbecco's modified Eagle's medium (DNEM) (wt/vol)/1% bovine serum albumin/20 mM Hepes, pH 7.4]. All potentials were defined relative to a Ag/AgCl reference electrode. Spectroscopic data were obtained with a Hewlett-Packard 8452A diode-array spectrophotometer.

Cell Studies. Bovine aortic endothelial cells (provided by P. D'Amore, Children's Hospital, Boston, Mass.) were maintained in Dulbecco's minimal essential media (DMEM) supplemented with 10% (vol/vol) calf serum (HyClone). Polypyrrole and control surfaces were assembled in a six-well chamber modeled after the Bionique chamber (Gabridge, M. G., In Vitro 17, 91–97 (1981)). To analyze effects on cell attachment, cells were plated (15,000 cells per $cm^2$) in serum-free medium on surfaces precoated with FN (10 $\mu g/cm^2$), as described in Ingber, D. E., *Proc. Natl. Acad. Sci. USA* 87, 3579–3583 (1990); and Mooney, D., et al., *J. Cell. Physiol.* 161, 497–55 (1992). Cells were allowed to attach for 10 minutes before a potential of –0.5 V was applied. Cells were glutaraldehyde-fixed 4 hours later, stained with Coomassie brilliant blue (Ingber, D. E., *Proc. Natl. Acad. Sci. USA* 87, 3579–3583 (1990); Sigma), and photographed on a Nikon Diaphot microscope under Hoffman optics.

To analyze effects on cell growth, serum-starved (0.4% calf serum for 2 days) cells monolayers were trypsinized and plated (15,000 cells per $cm^2$) on FN-polypyrrole or similarly coated Petri dishes in DMEM with 10% calf serum or in a chemically defined medium, consisting of DMEM supplemented with transferrin (5 $\mu g/ml$; Collaborative Research), high density lipoprotein (10 $\mu g/ml$; Cappel), 1% bovine serum albumin, and fibroblast growth factor (5 ng/ml; supplied by Takoda, Osaka) (Ingber, D. E. (1990) *Proc. Natl. Acad. Sci. USA* 87, 3579–3583.) For these experiments, −0.25 V rather than −0.5 V was used because cell lysis was observed in a previous study when −0.6 V was applied to indium trioxide surfaces (Shinohara, H., Kojima, J. Yaoita, J. & Alzawa, M. (1989) *Bioelectrochem. Bioenerg.* 22, 23–35). Effects on DNA synthesis were measured by quantitating nuclear incorporation of 5-bromo-2'-deoxyuridine (BrdUrd; Amersham) with a commercially available fluorescence assay (Amersham RPN20) except that rhodamine-conjugated goat IgG directed against mouse IgG Fc (Cappel) was used as the secondary antibody. The potential (0.25 V) was applied from 15 to 20 hours of culture, the time when these $G_0$-synchronized cells begin to reenter S phase, BrdUrd (3 µg/ml) was included only during this 5 hour period. Total number of cells and labeled nuclei were counted in four random fields (at×200; >50 cells per field) by using the phase-contrast and fluorescence capabilities of a Nikon Diaphot inverted microscope. Cell viability was quantitated with an assay (Live/Dead viability/cytotoxicity assay; Molecular Probes) that is based on the cellular incorporation of two fluorophores, calcein acetoxymethyl ester (viable cells) and ethidium homodimer (nonviable cells).

Results

The electrochemical synthesis resulted in formation of uniform films of polypyrrole on indium tin oxide-coated glass substrates. Film thicknesses were estimated from the amount of charge passed during electrodeposition (Wernet, W. & Wegner, W., *Makromol. Chem.* 188, 1465–1475 (1987)) and were ~0.1 µm. Polypyrrole obtained via electrochemical synthesis was in its oxidized state as a polycation with dopant anions to balance the charge (FIG. 1) and was able to be cycled between its charged and neutral forms electrochemically in culture medium, as shown by a cyclic voltammogram of polypyrrole in serum-free culture medium, at a scan rate of 50 mV/sec. The oxidation state of polypyrrole was monitored by UV/visible spectroscopy in its native oxidized state under no potential, reduced by application of −0.25 V, or −0.5 V. A broad peak near 800 nm associated with the bipolarons (Scott, J. C., et al., *Synth. Met.* 9, 165–172 (1984)) was present in the oxidized polymer. Application of −0.5 V switched polypyrrole to its neutral state, as indicated by the disappearance of the peak near 800 nm and the appearance of a separate peak near 370 nm. This latter peak has been previously shown to be characteristic of the neutral polymer (Genies, E. M., et al., *J. Electroanal. Chem.* 191, 111–126 (1985)). At −0.25 V, the spectrum fell between those of the oxidized and neutral states. The polymer spectra stabilized within 30 seconds after the potential was applied. When the reduction potential was removed, the neutral polymer reverted completely to its oxidized state within 30 seconds. This phenomenon has been observed by others as well (Li, Y., et al., *Synth. Met.* 28, C127–C132 (1989)).

Bovine aortic endothelial cells attached poorly and did not extend on uncoated polypyrrole when cultured in serum-free medium. In contrast, both cell attachment and spreading were observed when the oxidized polymer films were pre-coated with FN, an extracellular matrix molecule that adsorbs to surfaces and mediates binding to specific cell surface integrin receptors (Hynes, R. O., *Cell* 48, 549–554 (1987)). However, when cells were plated on FN-polypyrrole films that were converted to their neutral state, the cells attached but they remained round. Cell rounding was also observed with 1 hour when the electrical potential (−0.5 V) was applied to spread cells cultured for 4 hours on oxidized FN-polypyrrole before reduction. Cell rounding was not a result of cell injury since the viability of round cells on neutral FN-polypyrrole was similar to that on FN-coated Petri dishes (91±2% verses 99±1%, respectively). Thus, the observed effects on cell shape appeared to result from some process associated with polypyrrole reduction. Cell retraction and rounding could be due to release of substrate-adsorbed FN attachment molecules (i.e., detachment of cell anchors) following application of an electrical potential. Yet when polypyrrole that was coated with $^{125}$I-labeled FN was reduced by similar means, no significant release of adsorbed protein was observed. Cells were not included in these experiments, however, and thus local removal of FN anchors beneath the cells due to cell tractional forces remains a possibility.

Figure 2:
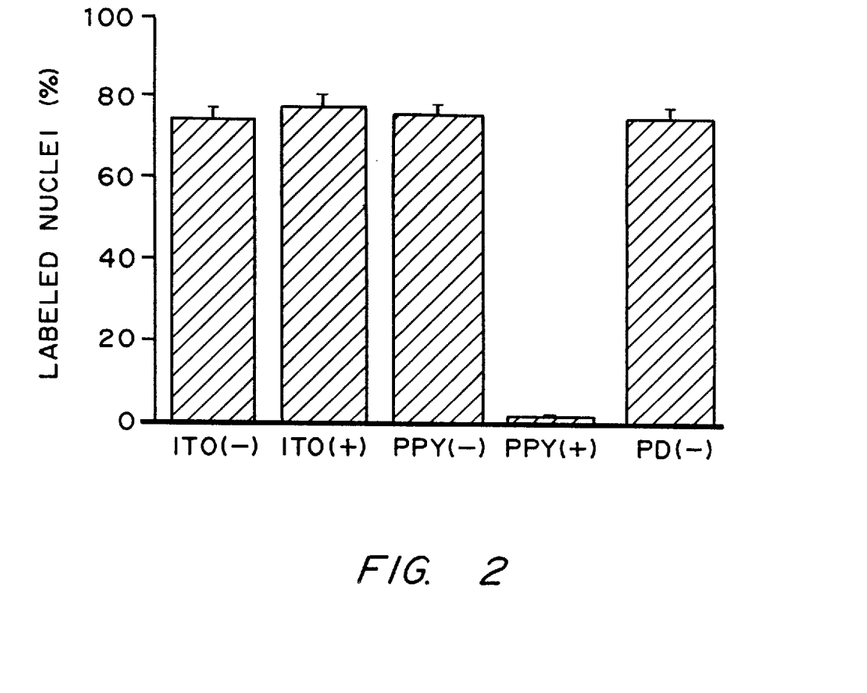
FIG. 2 is a graph of DNA synthesis in cells cultured in serum-containing medium on various FN-coated substrata: ITO (−), ITO (+), polypyrrole (−), polypyrrole (+), and PD (−), in the absence (−) or presence (+) of an applied electrical potential (−0.25 V). Data are presented as mean±standard error of the mean. ITO stands for indium tin oxide electrode, PPY for polypyrrole, PD for Petri dish. Cell viability was greater than 90% under all conditions.

Cell shape and growth have been shown to be tightly coupled in many anchorage-dependent cells (Folkman, J., et al., *Nature (London)* 273, 345–349 (1978); Ben-Ze'ev, A., et al., *Cell* 21, 365–372 (1980); Ingber, D. E., *Proc. Natl. Acad. Sci. USA* 87, 3579–3583 (1990); Mooney, D., et al., *J. Cell. Physiol.* 161, 497–505 (1992); Ingber, D. E., et al., *J. Cell Biol.* 109, 317–330 (1989)). Similarly, these experiments show that cell retraction induced by applying an intermediate electrical potential (−0.25 V) to FN-polypyrrole provided control over cell cycle progression (FIG. 2). Approximately 75% of cells cultured in serum-containing medium on FN-coated Petri dishes, indium tin oxide, or oxidized polypyrrole spread normally and entered S phase synchronously 15–20 hours after plating. Applying −0.25 V to indium tin oxide had little effect on either cell growth or form. In contrast, few cells (<2%) synthesized DNA when the same electrical potential was used to switch the FN-polypyrrole to its neutral state and promote cell retraction. Similar results were obtained when chemically defined, serum-free medium was utilized, except that labeling indices were slightly lower (date not shown). These effects were not due to cell death, since >90% of the cells remained viable on the neutral FN-polypyrrole, as determined by quantitating incorporation of the vital dye calcein acetoxymethylester.

EXAMPLE 2

Effect on Balb/c 3T3 Mouse Fibroblasts (ATCC 6587) of Reduction and Oxidation of Substratum of Fibronectin-Coated Polypyrrole Polymerizations: Chemical synthesis of polypyrrole was carried out based on a method by Gregory, R. V., W. C. Kimbrell and H. H. Kuhn, 1989, Synth. Met., 28: C823–C835, which was modified in order to form uniform coatings on substrates while maintaining reasonable transparency. The substrates used were polystyrene petri dishes (Falcon) and polystyrene tissue culture dishes (Corning Inc., Corning, N.Y. 14831). Pyrrole (Kodak Laboratories, Rochester, N.Y.) was passed through an activated alumina column until it became colorless. An aqueous solution of ferric chloride hexahydrate (0.018M, Mallinckrodt Specialty Chemicals Co., Chesterfield, Mo. 63017), p-toluene sulfonic acid (0.026M, Fluka Chem. Corp., Ronkonkowa, N.Y.), and purified pyrrole (0.006M) was added to beakers containing the substrates. The color of the solution turned from light yellow to dark green/black during the synthesis of polypyrrole. After two hours, the substrates were removed from the solution, rinsed several times with water, and dried in air at room temperature, as described in Wong, et al., *Polymer Preprints*, 34(2), 60–61, August 1993, American Chemical Society, incorporated herein by reference.

Electrochemical synthesis of polypyrrole was carried out in an electrochemical cell containing an optically-transparent indium tin oxide (ITO) anode (Delta Technologies, Stillwater, Minn.), platinum mesh counter electrode, and a pseudo Ag wire reference electrode. Electrodeposition (AFRDE4 bipotentiostat, Pine Instruments Co., Grove City, Pa. 16127) was performed in a solution of purified pyrrole (0.1M), tetraethylammonium-p-toluene sulfonate (0.1M, Alfa Products, Ward Hill, Mass. 01835), highly pure water (0.5 v/v %) and acetonitrile. Polypyrrole films were made potentiostatically at 0.8 V (vs. Ag wire) until about 150 m$^c$/cm$^2$ was passed, which corresponded to a thickness $\leq 1$ μm.

Polymer Characterization: Sheet resistances of the chemically formed polypyrrole were measured using a four-point probe meter (Four Dimensions, Model 101). Conductivity was calculated from sheet resistance and thickness measurements. The thickness of the chemically synthesized films were determined from a calibration curve of absorption at 950 nm vs. thickness for the electrochemically formed films determined with a Sloan Dektak IIA profilometer (Veeco Instruments, Inc., Plainview, N.Y. 11803). Spectroscopic data were obtained using an Oriel Instaspec model 250 spectrometer (Stratford, Conn., 06497). Conductivity of electrochemically synthesized polypyrrole was determined by the van der Pauw method (van der Pauw, L. J. 1958. Phillips Res. Repts. 13: 1–9) after the film had been removed from the anode. A Ramé-Hart goniometer (Ramé-Hart, Mountain lakes, N.J.) was used to measure static contact angles of water on the various samples. A minimum of 10 measurements were made for each sample.

Protein adsorption: Fibronectin (FN) was used as a model protein and its adsorption was quantitated according to the method of Ingber, D. E. *Proc. Natl. Acad. Sci. USA*. 87: 3579–3583 (1990), with conditions which maximize the adsorption efficiency. Various amounts of human serum FN (Cappell Laboratories Durham, N.C.) were mixed with $^{125}$I-labeled FN (ICN Radiochemicals, Inc. Costa Mesa, Calif. 92626) and dissolved in 0.1M carbonate buffer (pH 9.4) and applied at densities of 1, 10, 100, and 1000 ng/cm$^2$. Samples were tested in duplicate in a 12-well chamber. 100 μl of FN solution was added to the chamber wells and allowed to adsorb for 24 hours at 4° C. Wells were washed twice with Dulbecco's phosphate-buffered saline (Gibco/BRL Grand Island, N.Y. 14072). The samples were removed from the chamber; and the supernatant, washes, and samples were counted in a gamma counter (LKB-Wallace CliniGamma, Model 1272, Division of Pharmacia, Md.).

Cell culture: Cell attachment of Balb/c 3T3 mouse fibroblasts (ATCC 6587) was performed both in the presence and absence of calf serum. In a typical experiment, a cell suspension in Dulbecco's Modified Eagle Medium (DMEM, Gibco) supplemented with 10% calf serum (Hyclone Laboratories Inc., Logan, Utah 84321), 100 units/ml of penicillin (Gibco), and 100 μg/ml of streptomycin (Gibco) were plated onto dishes at a density of 5×10$^4$ cells/cm$^2$.

The electrochemically synthesized polypyrrole samples were assembled in a 6-well cell chamber. The polypyrrole surfaces were sterilized via exposure to UV-irradiation for 30 minutes. The tissue culture polystyrene was used as received from the manufacturer. In order to minimize non-specific binding interactions with the polystyrene bacteriologic petri dishes, the dishes were preincubated for 1 hour with DMEM containing 1% bovine serum albumin (Sigma, St. Louis, Mo.). Following a 4 hour incubation time (37° C., 5% CO$_2$), the cells were carefully washed with phosphate-buffered saline (PBS) to remove unattached cells. The attached cells were then removed by trypsinization. The cells from the wash and trypsinization were counted with a Coulter Counter Model Z$_F$(Coulter Electronics, Inc., Hialeah, Fla. 33012). Attachment was determined by the counts of the trypsinized cells divided by the total counts from the wash and the trypsinized cells.

Morphological analysis: Cells were fixed with glutaraldehyde and were observed under a phase-contrast microscope (Nikon TMS, Type 104, Nikon Inc., Melville, N.Y. 11747). Projected cell area was determined by staining the fixed cells with Coomassie blue and using a computerized image analysis system as described in Ingber, D. E., *Proc. Natl. Acad. Sci. USA* 87: 3579–3583 (1990). A minimum of 50 randomly selected cells were analyzed for each condition.

Results

Polypyrrole can be synthesized either electrochemically or chemically. Since it was not known which method would produce better materials for cell culture, both methods were examined. The substrates for the chemically synthesized polypyrrole were tissue culture (TC) and bacteriologic grade (PD) polystyrene dishes. The former had been glow discharge-treated rendering them hydrophilic; the latter were untreated and hence are hydrophobic. These surfaces were chosen with the cell studies in mind. A TC dish is considered to be standard in mammalian cell culture, whereas a PD dish is a surface which is relatively non-adhesive for mammalian cells. These experiments examined how the cell interaction changed after a thin film of polypyrrole was deposited onto the surfaces.

The thickness of the polypyrrole coating made via the chemical oxidative method was estimated to be about 700 A from a calibration curve of 950 nm absorbances versus actual thicknesses of polypyrrole on glass and platinum-coated glass slides measured with the Dektak. The absorption spectra showed a peak centered around 950 nm which confirmed that both the electrochemically and chemically formed polypyrrole were in their oxidized states. These spectra were in agreement with other studies examining the optical properties of oxidized polypyrrole. Diaz, A. F. and K. K. Kanazawa. ed. 1983. 417–441, in Miller: Extended Linear Chain Compounds. Plenum Press, New York.

Conductivity measurements (Table I) further confirmed that the polypyrrole thin films were in the oxidized state. An increase of 16 orders of magnitude in conductivity was observed after the polypyrrole was chemically deposited onto the TC and PD surfaces. The differences in wettability between the bare surfaces and after they have been coated with polypyrrole was another indication that there is a uniform coating of the polypyrrole.

TABLE I

Conductivity and Contact Angle Results

|  | Conductivity (Ω-cm)$^{-1}$ | Contact angle (°) |
|---|---|---|
| PD | 10$^{-15}$ | 81 ± 6 |
| TC | 10$^{-15}$ | 55 ± 5 |
| PPY/PD | 30 | 71 ± 5 |
| PPY/TC | 30 | 71 ± 4 |
| PPY/ITO | 1 | 73 ± 5 |
| ITO | 800 | 55 ± 6 |

Figure 3:
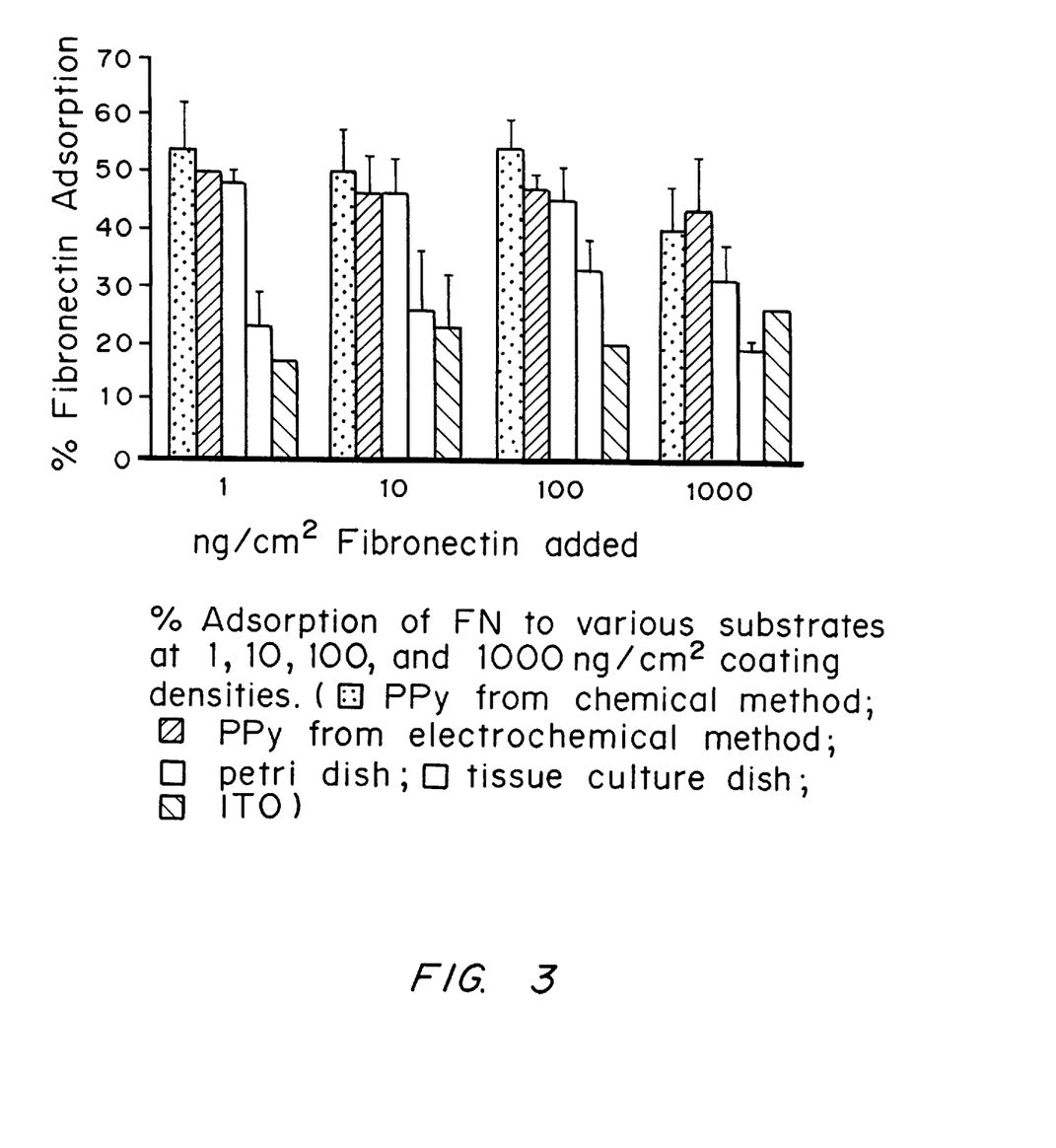
FIG. 3 is a graph of the percent adsorption of fibronectin (FN) at 1, 10, 100 and 1000 ng/cm$^2$ coating densities to substrates coated with polypyrrole using a chemical method (dark bar), coated with polypyrrole with an electrochemical method (//), a petri dish (−), a tissue culture dish ( ), and ITO (\\).

PD - Tissue culture grade polystyrene dishes
TC - Bacteriologic grade polystyrene dishes
PPY/PD - Polypyrrole deposited onto PD
PPY/TC - Polypyrrole deposited onto TC
PPY/ITO - Polypyrrole deposited onto optically transparent indium tin oxide anode
ITO - optically transparent indium tin oxide anode Since FN is a 220 kD glycoprotein which has been well-established as a cell adhesion protein (it adsorbs to a surface and mediates cell attachment), the experiments evaluated the adsorption of FN onto polypyrrole. FIG. 3 shows that for various initial coating densities, FN does not adsorb to polypyrrole. Furthermore, the amount of FN adsorbed appeared to be similar for polypyrrole synthesized chemically and electrochemically and is comparable to adsorption to the petri dish. A significantly smaller amount of FN adsorbed to TC and to PD. It was necessary to see how cells attached to the various surfaces in order to better evaluate the polypyrrole thin films.

Fibroblasts were chosen because they are anchorage-dependent cells, i.e., they need to attach and spread to a surface in order to survive. Furthermore, they are available as a stable immortal cell line. Cell attachment studies have shown that fibroblasts attach and spread to polypyrrole thin films both in the presence and absence of serum but spread to a degree intermediate between tissue culture polystyrene and bacteriologic petri dishes.

These results demonstrated that proteins adsorb to thin films of oxidized polypyrrole and that cells exhibit a normal response, such as attachment and spreading, when cultured on polypyrrole.

Modifications and variations of the methods and compositions described herein will be obvious to those skilled in the art from the foregoing detailed description and are intended to come within the scope of the appended claims.

We claim:

1. A method for altering the differentiation of anchorage dependent cells comprising binding cell surface receptor-specific attachment molecules of defined types and in a defined density to a surface consisting of an electrically conducting polymer, attaching anchorage-dependent cells to the cell surface receptor-specific attachment molecules on the electrically conducting polymer surface, and applying a voltage in an effective amount to change the oxidation state of the electrically conducting polymer thereby to alter the differentiation as a function of the type and density of the attachment molecules and applied voltage, wherein the anchorage dependent cells are selected from the group consisting of animal cells and plant cells.

2. The method of claim 1 wherein the electrically conductive polymer is selected from the group consisting of polyacetylene, polyaniline, polypyrrole, polythiophene, poly(phenylenesulfide), poly(phenylenevinylene), copolymers and blends thereof.

3. The method of claim 1 wherein the cells are dissociated mammalian cells.

4. The method of claim 1 wherein the polymer is coated onto a device or structure for cell culture.

5. The method of claim 1 wherein the polymer is coated onto, or used to form, a device or structure for implantation in the body.

6. The method of claim 5 wherein the device or structure is selected from the group consisting of sutures, bone screws, nails, plates, tubes, sheets, films, stents, and scaffolds for tissue engineering.

7. The method of claim 5 further comprising, following binding cell surface receptor-specific attachment molecules and prior to applying a voltage, implanting the polymeric material into a patient in need of treatment, wherein applying a voltage to the material alters healing of a wound in the body of the patient wherein the alteration is to enhance.

8. The method of claim 5 further comprising, following binding cell surface receptor-specific attachment molecules and prior to applying a voltage, implanting the polymeric material into a patient in need of treatment, wherein applying a voltage to the material alters formation of adhesions in the body of the patient, wherein the alteration is to decrease.

9. The method of claim 5 further comprising, following binding cell surface receptor-specific attachment molecules and prior to applying a voltage, implanting the polymeric material into a patient in need of treatment, wherein applying a voltage to the material alters differentiation and organ function in the body of the patient, wherein the alteration is to stimulate.

10. The method of claim 5 further comprising, following binding cell surface receptor-specific attachment molecules and prior to applying a voltage, implanting the polymeric material into a patient in need of bone repair or regeneration, wherein applying a voltage to the material alters bone repair or regeneration in the body of the patient, wherein the alteration is to enhance.

11. The method of claim 5 further comprising, following binding cell surface receptor-specific attachment molecules and prior to applying a voltage, implanting the polymeric material into a patient in need of nerve repair or regeneration, wherein applying a voltage to the material alters nerve repair or regeneration in the body of the patient, wherein the alteration is to enhance.

12. The method of claim 1 wherein the attachment molecules are selected from the group consisting of gelatin, albumin, fibronectin, laminin, carbohydrates, asialoglycoproteins, lectins, growth factors, low density lipoproteins, heparin, poly-lysine, thrombin, vitronectin, fibrinogen, peptides, and mixtures thereof.

13. The method of claim 12 wherein the peptides incorporate binding sites selected from the group consisting of R G D, L I G R K K T (SEQ ID NO: 1), and Y I G S R (SEQ ID NO: 2).

14. The method of claim 1 wherein the attachment molecules are selected from the group consisting of thrombospondin, entactin, proteoglycans, glycosaminoglycans, and mixtures thereof.

15. The method of claim 1 wherein the conducting polymer is coated onto a device or structure formed of a biodegradable polymer.

16. A device or structure for altering the differentiation of anchorage dependent cells comprising:

an electrically conductive polymer surface;

cell surface receptor-specific attachment molecules of defined types bound to the electrically conductive polymer surface in a defined density; and a means to apply a voltage across the electrically conductive polymer surface, wherein the means is electrically connected with the polymer, wherein the effect of the voltage on the differentiation of the cells attached to the polymer surface is altered as a function of the type and density of the attachment molecules.

17. The device or structure of claim 16 wherein the electrically conductive polymer is selected from the group consisting of polyacetylene, polyaniline, polypyrrole, polythiophene, poly(phenylenesulfide), poly(phenylenevinylene), copolymers and blends thereof.

18. The device or structure of claim 16 wherein the attachment molecules are selected from the group consisting of gelatin, albumin, fibronectin, laminin, carbohydrates, asialoglycoproteins, lectins, growth factors, low density lipoproteins, heparin, poly-lysine, thrombin, vitronectin, fibrinogen, peptides, and mixtures thereof.

19. The device or structure of claim 18, wherein the peptides incorporate binding sites selected from the group consisting of R G D, L I G R K K T (SEQ ID NO: 1), and Y I G S R (SEQ ID NO: 2).

20. The device or structure of claim 16, wherein the attachment molecules are selected from the group consisting of thrombospondin, entactin, proteoglycans, glycosaminoglycans, and mixtures thereof.

21. The device or structure of claim 16, wherein the polymer is coated onto a device or structure for cell culture.

22. The device or structure of claim 16, wherein the polymer and the means to induce a voltage across the polymer are connected by electrodes.

23. The device or structure of claim 16, wherein the electrically conductive polymer has had a change in its oxidative state due to an applied voltage across the polymer.

24. The device or structure of claim 16, further comprising anchorage dependent cells attached to the cell surface receptor-specific attachment molecules.

25. The device or structure of claim 24 wherein the anchorage dependent cells are dissociated mammalian cells.

26. The device or structure of claim 16 wherein the device is used for implantation, and wherein the device is selected from the group consisting of sutures, bone screws, nails, plates, tubes, sheets, films, stents, and scaffolds for tissue engineering.

* * * * *